United States Patent
Roskin et al.

[11] Patent Number: 6,106,461
[45] Date of Patent: *Aug. 22, 2000

[54] SELF DIAGNOSTIC DEVICE FOR VAGINAL SECRETION

[75] Inventors: Amy C. Roskin, Box 770041, Coral Springs, Fla. 33065; Joanne M. Richards, Box 77041, Coral Springs, Fla. 33077

[73] Assignees: Amy C. Roskin; Joanne M. Richards, both of Tamarac, Fla.

[ * ] Notice: This patent is subject to a terminal disclaimer.

[21] Appl. No.: 09/119,718

[22] Filed: Jul. 20, 1998

Related U.S. Application Data

[63] Continuation of application No. 08/667,078, Jun. 20, 1996, Pat. No. 5,823,953.

[51] Int. Cl.⁷ ........................................................ A61B 5/00
[52] U.S. Cl. ........................ 600/309; 600/573; 600/584; 604/358
[58] Field of Search ..................................... 600/309, 362, 600/367, 300, 573, 584; 128/830; 604/358, 361, 362, 367; 422/68.1

[56] References Cited

U.S. PATENT DOCUMENTS

| | | |
|---|---|---|
| 2,664,879 | 1/1954 | Hardy . |
| 3,509,872 | 5/1970 | Truhan . |
| 5,063,930 | 11/1991 | Nucci . |
| 5,217,444 | 6/1993 | Schoenfeld . |
| 5,275,591 | 1/1994 | Mavinkurve . |
| 5,425,377 | 6/1995 | Caillouette . |
| 5,445,147 | 8/1995 | Schoendorfer et al. . |
| 5,823,953 | 10/1998 | Roskin et al. .......................... 600/367 |

*Primary Examiner*—Linda C. M. Dvorak
*Assistant Examiner*—Bryan Yarnell
*Attorney, Agent, or Firm*—Wilson Sonsini Goodrich & Rosati

[57] ABSTRACT

Self diagnostic devices and methods for detecting a physical condition of a female based on a property of a vaginal secretion of the female are provided. The device comprises: a region of the device which receives the vaginal secretion from a body of the female and changes in appearance based on whether the vaginal secretion has a selected physical property; and a mounting mechanism for mounting the region of the device on the body adjacent to and external from the vagina such that the region receives secretions from the vagina and does not substantially lose water or other volatile components of the vaginal secretion due to vaporization. The device can be used for convenient diagnosis of vaginal infections such as infections caused by yeast, bacteria, viruses and other microorganisms.

13 Claims, 1 Drawing Sheet

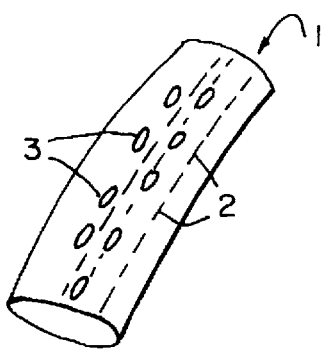
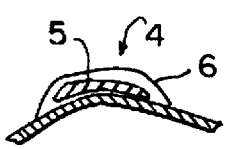
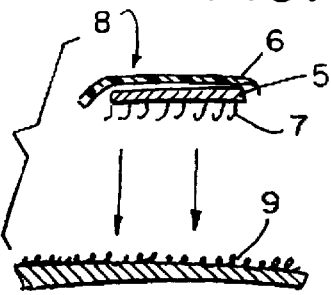
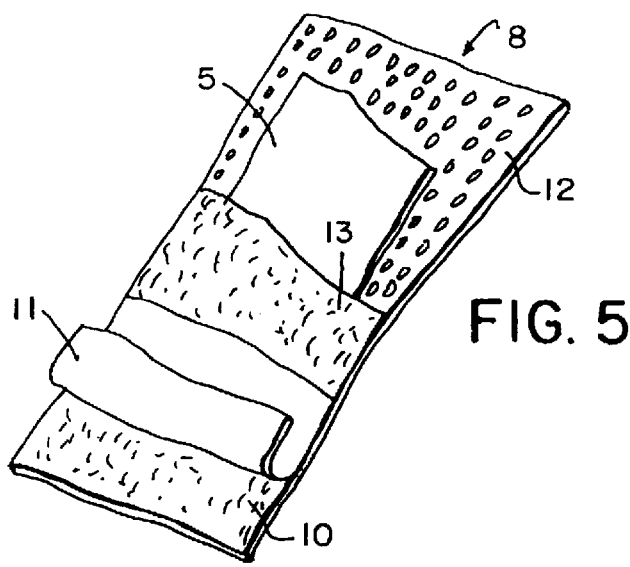
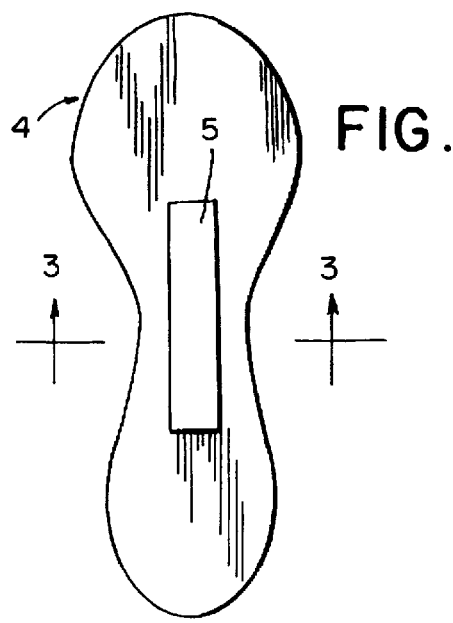
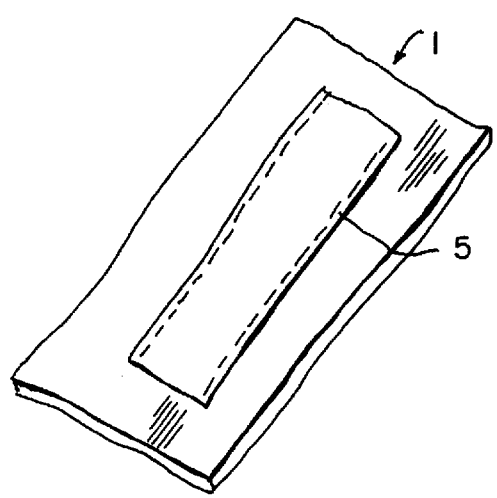

SELF DIAGNOSTIC DEVICE FOR VAGINAL SECRETION

This application is a continuation of U.S. patent application Ser. No. 08/667,078, filed Jun. 20, 1996, now U.S. Pat. No. 5,823,953.

BACKGROUND OF THE INVENTION

1. Field of the Invention

This invention relates to diagnosis of infection and more particularly to a method and apparatus for external measurement of the pH of vaginal secretion.

2. Background Art

Vaginal infections may be divided into two general categories, yeast infections which cause acid secretions with a pH below about 4.5 and non-yeast infections which cause secretions with a pH generally above 4.5.

A number of over the counter medicines are now available for treatment of vaginal yeast infections. The signs and symptoms of yeast infections are not readily distinguishable from other infections, although they comprise less than half of the infections Consequently, patients too often resort to self treatment with yeast medicine when it cannot possibly be effective. This may dangerously delay effective treatment.

U.S. Pat. No. 2,664,879 issued Jan. 5, 1954 to Hardy and U.S. Pat. No. 5,063,930 issued Nov. 12, 1991 to Nucci disclose devices for measuring vaginal pH internally with pH indicators carried on an instrument inserted into the vagina.

These have several disadvantages. Women generally object to any internal instrumentation. The sensitive tissues are vulnerable to reaction with many materials such as indicators. Sterility is a further concern. They do not lend themselves to home health care in conjunction with the over the counter medicine used for yeast infections.

SUMMARY OF THE INVENTION

It is accordingly an object of the invention to provide a method and apparatus for differentiating between yeast and non yeast vaginal infections that is more acceptable to women, safer, easier to use, and less expensive to produce.

The infections produce secretions which drain from the vagina. We have discovered that measurement of the pH of the secretions after they have left the body will effectively differentiate the two types of infections. Women are accustomed to absorbing fluids escaping from the vagina with catamenial pads, panty liners, and the like. The invention comprises pH indicating material attached or attachable to garments or devices ordinarily worn so as to absorb secretions. The pH indicating material is of the type that provide a color indicative of the pH of the fluid contacting it. This enables an untrained user to determine the pH of the secretions by simple visual reference to a color chart. There is less exposure to sensitive tissues for infection and toxicity problems.

These and other objects, features and advantages of the invention will become more apparent when the detailed description is studied in conjunction with the drawings in which like reference characters indicate like elements in the various figures.

BRIEF DESCRIPTION OF THE DRAWINGS

FIG. 1 is a perspective view of a pad of the invention.

FIG. 2 is a perspective view of a pantyliner embodying the invention.

FIG. 3 is a sectional view taken through line 3—3 of FIG. 2.

FIG. 4 is a sectional view of another embodiment of the invention.

FIG. 5 is a perspective view of another embodiment of the invention, with various layers partially broken away.

FIG. 6 is a perspective view of another pad of the invention.

DETAILED DESCRIPTION OF PREFERRED EMBODIMENTS

Referring now first to FIG. 1, a catamenial pad 1 may be of the type in common use or a thinner pad especially made for this purpose. Fibers or threads 2 comprised of pH indicating material such as cotton thread impregnated with pH indicating dye may be sewn onto the pad surface where they will become wetted by the vaginal secretions and change color to thereby disclose to the user the pH of the secretions. The pH indicator indicating pH at least in the range of pH 3.5–5.5. A color chart (not shown) may be included, such as on the wrapper, for comparison, along with instructions such as "this color indicates that your problem is not a yeast infection, see your doctor". Alternatively, spots of the dye 3 may be directly imprinted on the pad.

Referring now to FIGS. 2 and 3, a pantyliner of the invention comprises a conventional pantyliner 4 upon whose surface is securely attached a pH indicating paper strip 5. An overlay of a thin, transparent, water permeable and water insoluble plastic film 6 holds the strip in place and separates the strip from any sensitive body tissues that might react unfavorably to the pH indicating material. The secretions will diffuse through the film 6 and wet the indicating strip 5 to provide the color change visible through the transparent film. An example of a suitable film material would be ethylcellulose which is inert enough to be acceptable for oral medications.

Referring now to FIG. 4, a pH indicating strip 5, coated with a transparent, water permeable, water insoluble film 6 has affixed to the underside a layer of hook material 7 of the hook and loop fastener type that enables the combined device 8 to be attachable and detachable from a soft fabric having a loose surface texture 9 which may serve as the loop material for attachment. Certain garments, pads and pantyliners may have a texture of this nature without modification.

FIG. 5 shows another attachable, detachable pH indicating strip 8 having a pressure sensitive adhesive surface 10 protected with release paper 11. The release paper is stripped off and the strip 8 is removably adhered to the crotch of an undergarment. The indicating paper strip 5 is sandwiched between two layers of transparent plastic film, the outer, perforated film layer 12 and the inner film layer 13 that is carrying the adhesive. The perforations permit penetration of the secretions into the paper strip 5 while keeping the dye away from sensitive tissues.

FIG. 6 shows a catamenial pad 1 in which the pH indicating strip 5 is stitched in place.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention.

What is claimed is:

1. A self diagnostic device for detecting a physical condition of a female based on a property of a vaginal secretion of the female, the device comprising:

a region of the device which is capable of receiving the vaginal secretion from a body of the female and changes in appearance based on whether the vaginal secretion has a selected physical property; and a mounting mechanism for mounting the region of the device on the body adjacent to and external from the vagina such that the region receives secretions from the vagina and does not substantially lose water or other volatile components of the vaginal secretion due to vaporization.

2. A device according to claim 1 wherein the mounting mechanism includes an adhesive.

3. A device according to claim 1 wherein the mounting mechanism includes a hook material.

4. A device according to claim 1 wherein the mounting mechanism includes stitching.

5. A device according to claim 1 wherein the device further includes a transparent perforated barrier film over the region for preventing contact between the region and the body.

6. A device according to claim 1 wherein the region is in the form of fibers or threads stitched onto a wearable substrate.

7. A device according to claim 6 wherein the wearable substrate is selected from the group consisting of pantyliners and catamenial pads.

8. A self diagnostic device for detecting a physical condition of a female based on a property of a vaginal secretion of the female, the device comprising:

a region of the device including pH indicating material which is capable of receiving the vaginal secretion from a body of the female and changes in appearance based on a pH of the vaginal secretion; and a mounting mechanism for mounting the region of the device on the body adjacent to and external from the vagina such that the region receives secretions from the vagina and does not substantially lose water or other volatile components of the vaginal secretion due to vaporization.

9. A device according to claim 8 wherein the region includes pH indicating material for indicating a pH of the vaginal secretion between about pH 3.5 and 5.5.

10. A device according to claim 8 wherein the device further includes a water permeable barrier film over the pH indicating material for preventing contact between the pH indicating material and the body.

11. A device according to claim 8 wherein the pH indicating material includes dye imprinted on a wearable substrate.

12. A device according to claim 11 wherein the wearable substrate is selected from the group consisting of pantyliners and catamenial pads.

13. A self diagnostic method for detecting a physical condition based on a property of a vaginal secretion, the method comprising:

wearing a device adjacent to and external from a vagina of a body such that the device is positioned to receive secretions from the vagina, the device having a region which receives the secretion and changes in appearance based on whether the vaginal secretion has a physical property;

removing the device from adjacent to the vagina after a time for a sufficient quantity of vaginal secretions to be received by the device; and observing the region of the device in order to determine whether the region has changed in appearance so as to indicate that the vaginal secretion has the physical property.

* * * * *